United States Patent [19]

Young et al.

[11] 4,278,083
[45] Jul. 14, 1981

[54] FLOW REGULATING DEVICE FOR ARTERIAL CATHETER SYSTEMS

[76] Inventors: James E. Young, 2080 E. 4675 South, Salt Lake City, Utah 84117; Ralph S. Walker, 9767 N. 6530 West, Highland, Utah 84003; James R. Chidester, Rte. 1, Box 150 B, American Fork, Utah 84003

[21] Appl. No.: 46,234

[22] Filed: Jun. 7, 1979

Related U.S. Application Data

[63] Continuation-in-part of Ser. No. 920,500, Jun. 29, 1978, Pat. No. 4,192,303.

[51] Int. Cl.³ .................. A61M 5/00; F16K 51/00
[52] U.S. Cl. .................. 128/214 R; 128/214 F; 251/117; 251/335 R
[58] Field of Search ............ 128/214 R, 274, 227; 251/117, 333, 38, 335 R; 138/45, 46

[56] References Cited

U.S. PATENT DOCUMENTS

| | | | |
|---|---|---|---|
| 3,298,367 | 1/1967 | Bergman | 128/214 R |
| 3,675,891 | 7/1972 | Reynolds et al. | 128/214 R X |
| 4,192,303 | 3/1980 | Young et al. | 128/214 R |

Primary Examiner—Frank A. Spear, Jr.
Attorney, Agent, or Firm—Terry M. Crellin; B. Deon Criddle

[57] ABSTRACT

A flow regulating device provides continuous, regulated flow of a medical fluid, as well as intermittent, manually controlled larger flows of fluid to a catheter system. Such apparatus includes a control member having an inlet means adapted to be connected by tubing to a source of medical fluid and an outlet means adapted to be connected by tubing to a catheter. A flexible conduit defines at least a portion of a first passage between the inlet means and outlet means of the control member. A cylindrical, hollow extension extends from the outlet means coaxially within and to about the midsection of the flexible conduit. Positioned in the flexible conduit is valve means adapted to open when the conduit is squeezed, thereby providing the larger, intermittent, manually controlled flow of fluid to the catheter system, and to automatically close when the conduit is released. A second passage in the control member connects the inlet and outlet means, and in combination with flow restriction means therein, provides the continuous, regulated flow of fluid to the catheter system.

12 Claims, 6 Drawing Figures

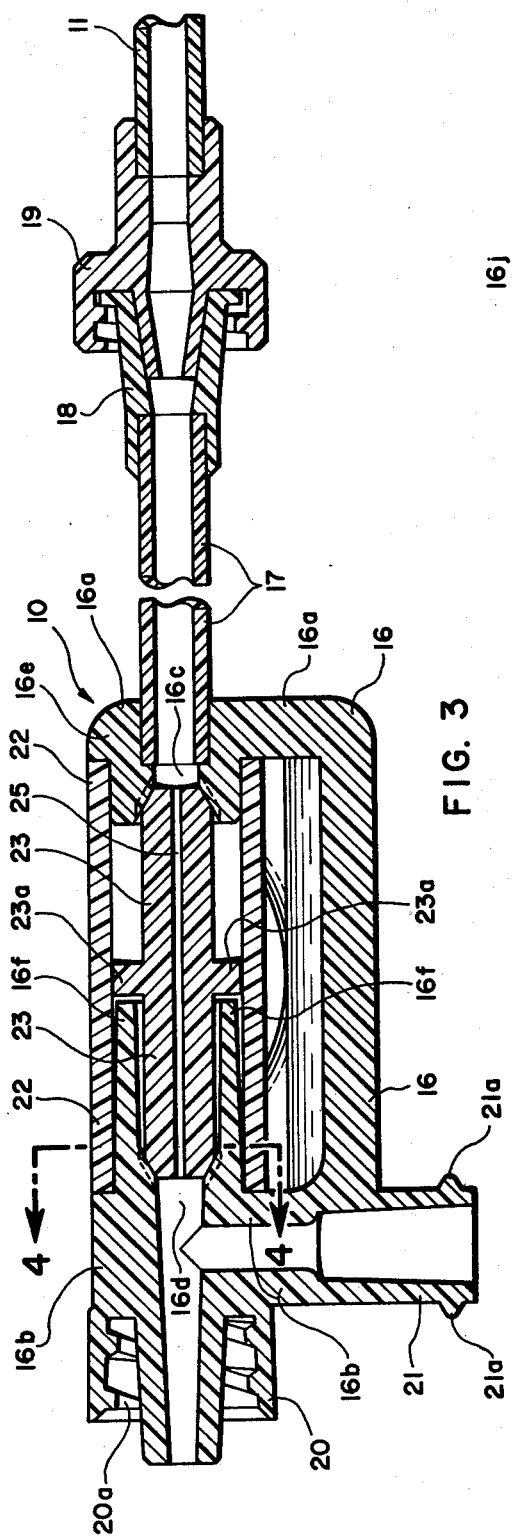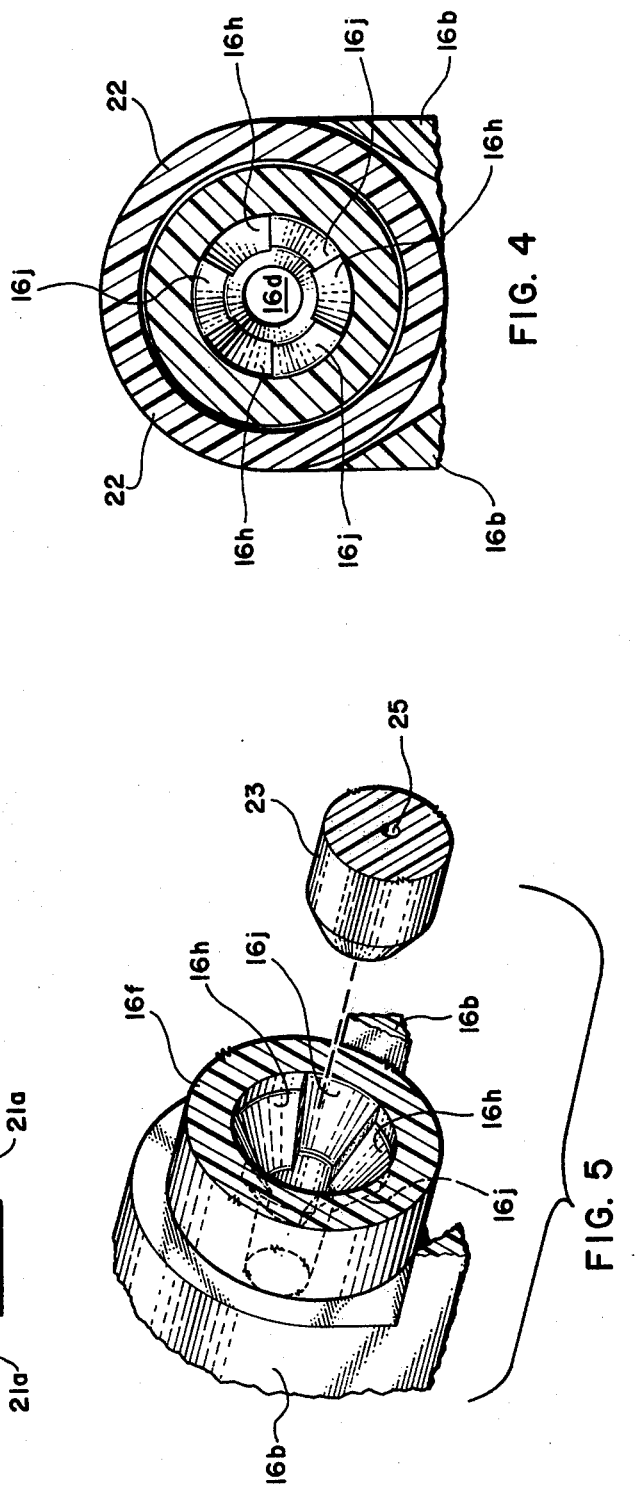

FLOW REGULATING DEVICE FOR ARTERIAL CATHETER SYSTEMS

BACKGROUND OF THE INVENTION

RELATED APPLICATION

This application is a continuation-in-part of my co-pending application Ser. No. 920,500, filed June 29, 1978, now Pat. No. 4,192,303.

FIELD

This invention pertains generally to intravenous catheter systems used in monitoring arterial functions and in the infusion of medical fluids to a patient. In particular, the invention relates to flow apparatus for controlling the flow of fluid at a desired continuous rate and to provide for intermittent, manually controlled larger flows of fluid to rapidly flush the catheter system.

STATE OF THE ART

Intravenous catheterization is a very useful procedure available for clinical monitoring of blood system and related parameters including arterial pulse waveform, stroke volume, heart rate, cardiac output, duration of systole, and systolic, diastolic and mean pressures. In addition, blood can be withdrawn for blood gas analysis.

To provide reliable operation over periods which may amount to several days, it has been found essential to flush the catheter continuously during its use with a regulated, continuous infusion of a relatively small flow of a liquid to prevent occlusion of the intravascular end of the catheter by blood coagulation. Continuous flushing systems have been proposed which utilize capillary tubes as flow resistors, with the flushing solution flowing therethrough under pressure. See, for example, U.S. Pat. No. 3,675,891 issued to Gordon S. Reynolds, et al. on Sept. 18, 1970, and an article appearing on pages 675-678 of the Journal of Thoracic and Cardiovascular Surgery, Volume 57, No. 5, May 1969.

Generally, the prior systems employed an objectionable large amount of apparatus including numerous stopcocks, with resulting loss of fidelity in the operation of the system. The device disclosed in U.S. Pat. No. 3,675,891 overcomes many of the deficiencies inherent in the earlier systems by providing a relatively small unitary piece of apparatus which was constructed so as to eliminate the use of all stopcocks. A resilient valve was provided to control a bypass around the capillary flow resistor, with the valve being operated by manually pulling a valve stem which extends longitudinally from the apparatus. The valve and stem system of such device, however, has certain drawbacks. For example, the protruding stem is subject to entanglement in tubing, bedding, or other paraphenalia resulting in possible undesired opening of the valve or breakage of the valve stem so as to preclude proper operation of the device. The valve stem can also be broken by pulling the stem to one side or the other rather than longitudinal, and the valve has also been found to occasionally fail in the open position. In addition, the valve and stem system is generally difficult to operate with one hand, and for all practical purposes, requires two-handed manipulation.

OBJECTIVES

The principal objective of the present invention is to provide an improved regulating device which is reliable and easy to operate, as well as being simple in construction. A particular objective of the invention is to provide a small, streamlined device for connection in the catheter system which can be operated easily with one hand and which does not include stopcocks or stem actuated valves as in the devices of the prior art.

SUMMARY OF THE INVENTION

The above objectives are achieved in accordance with the present invention by providing a small, unitary, flow regulating device comprising a control member having an inlet means adapted to be connected to a source of a medical fluid and an outlet means adapted to be connected to an intravenous catheter. The control member is provided with a first passage connecting the inlet and outlet means for fluid flow communication therebetween, with at least a part of the first passage comprising a section of flexible conduit having valve control means positioned therein. A cylindrical, hollow, extension extends from the outlet means coaxially within and substantially to the midsection of the flexible conduit. The valve means is adapted to open and permit a flushing flow of liquid to pass through the first passage when the conduit is squeezed and to close and thereby stop the flushing flow of fluid when the conduit is released.

A second passage is provided in the control member. The second passage by-passes the valve means and connects the inlet and outlet means for flow communication therebetween. A flow restriction means is provided in the second passage to restrict the flow of fluid therethrough to a limited, continuous flow under a given upstream pressure.

Additional objects and features of the invention will become apparent from the following detailed description of a preferred embodiment, taken together with the accompanying drawing.

THE DRAWING

In the drawing:

FIG. 3 is a cross-sectional view taken along line 3—3 of FIG. 2;

FIG. 4 is a cross-sectional view taken along line 4—4 of FIG. 3, with the plug member removed to more clearly show the undercut slots in the beveled end of the flow passage in which the plug member is positioned;

FIG. 5 is a pictorial cross-section of the end of the flow passage taken along line 4—4 of FIG. 3, with the flexible conduit omitted and with the end portion of the plug member being shown longitudinally exploded from its normal position to show the undercut slots and the ribs of the beveled end portion of the flow passage;

DETAILED DESCRIPTION

Figure 1:
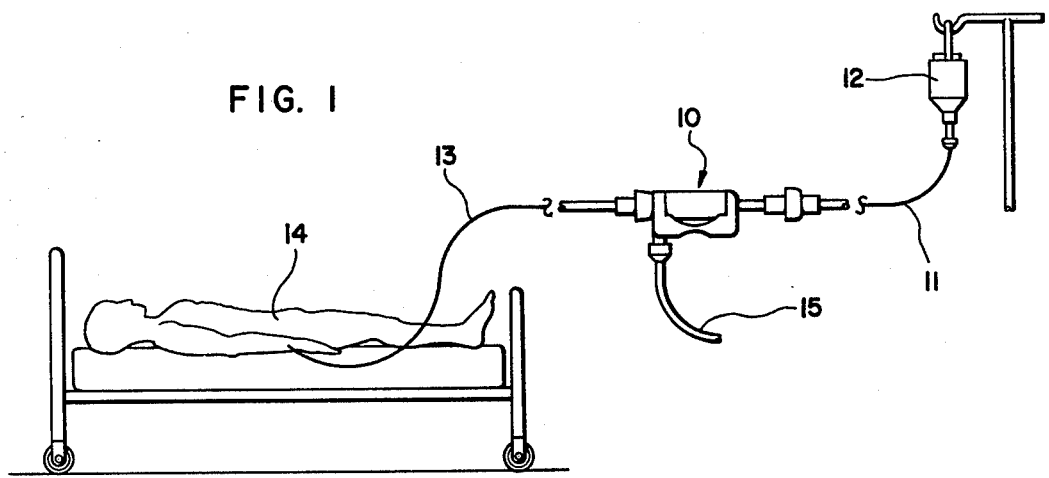
FIG. 1 is a diagramatic illustration of a device in accordance with this invention in operative association with a catheter system which is inserted into the arm of a patient, the device itself being exaggerated for purposes of illustration.

The device of the present invention is adapted to be incorporated in various catheter systems. As used throughout the specification and claims, the term "catheter systems" is meant to include systems using catheters, cannulas, or other tubes inserted into the arterial system of a patient and used to monitor arterial functions and parameters as well as withdrawing blood from or infusing medical fluids into the arterial system.

By way of example, the flow control device is shown in the drawing and will be described herein as incorporated into a catheter system for monitoring arterial pressure and recording of arterial pulse waveforms. The catheter used in such a system is very thin, having an inside diameter of about one-half millimeter. The catheter must be maintained in open and operable condition for transmitting pressure pulses. The tendency for a blood clot or other occlusion to form at the end of the catheter positioned within the arterial system is greatly reduced by continuously infusing a sterile solution into the arterial system through the catheter in an amount which will not harm the patient but will retard the formation of occlusions in the catheter. Generally, depending on the size of the patient, from about 2 cc to about 7 cc of solution per hour has been found to be safe and beneficial.

In accordance with the present invention, means are also provided for manually flushing the catheter system from time to time with a momentary increase in the flow of solution through the catheter. The increased flow of fluid clears the catheter of any clots or occlusions which have formed or are being formed. In addition, the increased flow of fluid permits rapid clearing of all air from the system during the installation of the catheter into the arterial system of the patient, as will be discussed more fully hereinafter.

A preferred embodiment of the flow control device is shown in the six figures of the drawing, with similar components of the device being identified with the same reference numeral. The device comprises a control member 10, which as shown in FIG. 1 is adapted to be connected by tube 11 to a supply of a medical fluid in container 12. The control member 10 is also connected by tube 13 to a catheter which has been positioned within the arm of a patient 14. Means are provided for connecting the control member 10, in fluid flow communication through tube 15, to diagnostic apparatus (not shown in the drawing) which is capable of monitoring various arterial functions such as those mentioned previously. A variety of diagnostic apparatus is well known to the medical art and does not, per se, constitute part of the present invention. As will be more fully described hereinafter, the means which are provided for connecting tube 15 to control member 10 can also be used for hypodermic injections to the patient and for withdrawing of blood samples from the patient.

Figure 2:
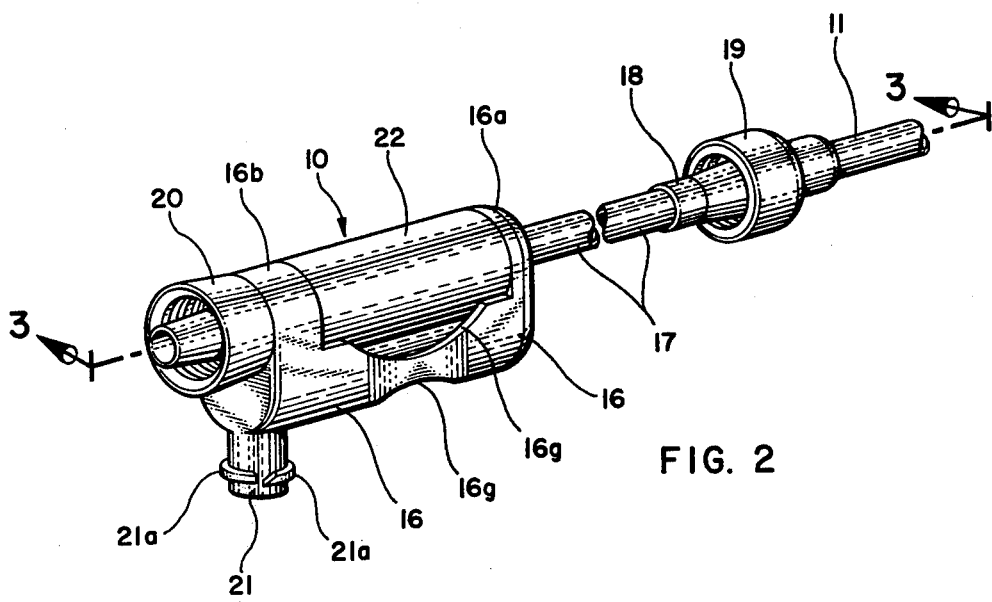
FIG. 2 is a perspective view of a preferred embodiment of the device.

The construction of the control member 10 is best shown in FIGS. 2-5, and will be described with reference thereto. As illustrated, the control member 10 consists of a body member 16 having upstanding end caps 16a and 16b, respectively, such that in side elevation, the body member 16 has a broad, generally U-shaped profile. The end cap 16a is provided with inlet means for connecting the control member 10 to the tube 11 which, in turn, is connected to a supply of medical fluid, such as the container 12 shown in FIG. 1. The inlet means as shown in FIGS. 2 and 3 comprises a short piece of tubing 17 which is securely affixed to the end cap 16a at one of its ends and has a male fitting 18 attached to its other end. The fitting 18 is adapted to releasably engage a female fitting 19 on the end of tube 11. Of course, the order of the fittings could be reversed, i.e., the female fitting could be attached to the tubing 17, with the male fitting being on the end of tube 11. Various types of fittings, some being, as illustrated, adapted for interlocking engagement between lugs on the male fitting and internal thread-like receptacles on the female fitting, and some being adapted for simple sliding engagement, are commercially available for use in the present invention.

The other end cap 16b is provided with outlet means which is adapted to be connected to an intravenous catheter by way of an appropriate tube, such as tube 13 shown in FIG. 1. As illustrated in FIGS. 2 and 3, the outlet means comprises a fitting 20 which is adapted for connection to a mutually corresponding fitting on a fluid conveying tube leading to the catheter. The fitting 20 can be any of various type fittings conventionally used for connecting medical tubing together or to other medical apparatus. As shown, the fitting 20 is of the type having an internally threaded receptacle 20a (FIG. 3) adapted to receive a male fitting having lugs thereon for engagement with the threads of the receptacle.

The outlet means at end cap 16b preferably also includes a second fitting 20, which, as shown, is a male fitting having side lugs 21a which are adapted to releasably engage the threads of a mutually corresponding fitting on a tube, such as tube 15 shown in FIG. 1, for connecting the control member 10 to diagnostic apparatus capable of monitoring various functions such as blood pressure, etc., as mentioned previously. The fitting 21 could be of the female type such a fitting 20; however, inasmuch as the fitting on the diagnostic apparatus is likely to be of the female type, and connecting tubing conventionally has a male fitting at one end and a female fitting at the other end, it is advantageous to make the fitting 21 of the male type, as shown.

A fluid flow passage connects the inlet and outlet means in the end caps 16a and 16b of body member 10. As best illustrated in FIGS. 2 and 3, the flow passage comprises bores 16c and 16d through the respective end caps 16a and 16b which are in flow communication with the tube 17 and fitting 20, respectively. The end cap 16a has an inwardly facing hub 16e, which is adapted to receive one end of a flexible conduit 22 in tight coaxial fit thereover. A cylindrical hollow extension 16f extends inwardly from the end cap 16b to a distance up to about midway between the end caps 16a and 16b. The other end portion of the flexible conduit 22 fits coaxially over the cylindrical extension 16f. As illustrated, the cylindrical extension 16f is tapered slightly from its free end to the end thereof which joins the end cap 16b. The diameter of the cylindrical extension 16f at the base thereof adjacent to the end cap 16b is sufficient to make a fluid tight seal with the other end of the flexible conduit 22. Thus, the conduit 22 connects the bores 16c and 16d for fluid flow communication therebetween, and together with the bores 16c and 16d of the end caps 16a and 16b forms a fluid flow passage connecting the inlet and outlet means in the end caps 16a and 16b of the body member 10.

A valve means is positioned within the flexible conduit 22 and is adapted to open and permit the intermittent, larger, flushing flow of fluid to pass through the flexible conduit 22 when the conduit 22 is squeezed, and to close when the squeezing action on the conduit 22 is terminated. Preferably, the valve means comprises a substantially cylindrical plug member 23 (FIG. 3) positioned coaxially within the flexible conduit 22. The plug member 23 has a raised band 23a thereabout intermediate its ends, with the band 23a having a sufficient diameter that its exposed surface forms a substantially flow tight seal with the interior wall of the flexible conduit 22, so that when the flexible conduit is not being squeezed, fluid is substantially completely prevented from flowing around the plug between the raised band 23a and the interior wall of flexible conduit 22. Preferably, the raised band 23a is located around the plug member 23 substantially equidistant from the ends of the plug member 23. In any case, the cylindrical extension 16f extends to a point adjacent to but slightly spaced from the raised band 23a. The portion of the plug member 23 on the upstream side of the raised band 23a, i.e., the portion of the plug member 23 which extends from the raised band to the end cap 16a, is of a reduced diameter and thus an open flow space 24 is formed between the flexible conduit 22 and that particular portion of the plug member 23. The portion of the plug member 23 on the downstream side of the raised band 23a has a sufficiently reduced diameter whereby such portion fits coaxially within the cylindrical hollow extension 16f with an open flow space 24a being formed between the interior surface of the cylindrical extension 16f and the downstream portion of the plug member 23.

When the flexible conduit 22 is subjected to a squeezing action in the vicinity of the raised band 23a, the seal between the raised band 23a and the interior wall of the flexible conduit 22 is broken, due to deformation of the flexible conduit 22 which creates flow channels extending across the raised band 23a. Fluid can then flow around the plug member 23 and through the flexible conduit 22. Upon termination of the squeezing action on the flexible conduit 22, the seal between the raised band 23a and the interior wall of the flexible conduit 22 is automatically re-established, thereby terminating the flow of fluid around the plug member 23. Advantageously, the base portion of the body member 16 has concave depressions 16g (FIG. 2) in the side thereof facing the flexible conduit 22 and the two sides thereof extending from the flexible conduit, respectively. The concave depressions form finger guides on each side of the control member 10 which aid in positioning one's fingers for squeezing the flexible conduit 22.

Figure 6:
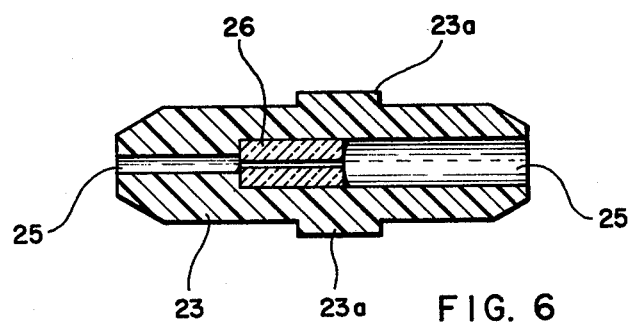
FIG. 6 is a vertical section of a modified version of the plug valve of FIG. 3.

A second passage is provided in the control member 10 for by-passing the valve means in the flexible conduit 22 and connecting the inlet and outlet means of body member 16. Such a by-pass passage could be routed through the body member 16 from the inlet means in end cap 16a to the outlet means in end cap 16b. Preferably, however, the second passage is combined in the valve means itself as shown in FIGS. 3 and 6. In the preferred mode, the plug member 23 is positioned concentrically in the flexible conduit 22 and is provided with a bore 25 extending longitudinally through the plug member 23 which by-passes the valve means in the flexible conduit 22.

Flow restriction means is provided in the second passage for limiting the amount of fluid passing through the second passage to a desired relatively small rate. As illustrated in FIG. 3, the flow restriction is advantageously provided by forming at least a portion of the bore 25 into a capillary section having a very small diameter in the order of several hundredths of a millimeter. As shown in FIG. 3, the bore 25 forms the capillary which extends the length of the plug member 23. The capillary is shown in FIG. 3 in greatly exaggerated proportions for purposes of clarity, since the capillary in reality is so small in diameter as to be practically invisible without the use of some type magnification. By incorporating capillary sections 25a of different diameters and lengths, a broad series of apparatus can be readily produced from which individually sized units can be chosen which will deliver the desired amount of fluid under the given upstream pressure which is to be utilized in the particular application.

In an alternate embodiment of the plug member 23 shown in FIG. 6, the flow restriction is provided by positioning a resistance element 26 in an oversize bore 25 of the plug member 23. The resistance element 26 comprises a marine-bore capillary tube, with the diameter of the bore in the element 26 being very small, in the order of hundredths of a millimeter. The bore in the element 26 of FIG. 6 is shown in greatly exaggerated proportions for purposes of illustration. To aid in positioning the marine-bore resistance element 26 in the bore 25 of plug member 23, the bore 25 has a downstream section having a reduced diameter as shown in FIG. 6. The capillary tube 26 is then forced into bore 24 from the upstream end thereof until it abuts the edges of the reduced diameter section of bore 25. The outside diameter of the resistance element 26 is sufficient so that a tight, non-leaking seal is made between the external surface of the element 26 and the bore 25.

Preferably, the second passage extending through the plug member 23, i.e., the bore 25 is coaxial with the longitudinal axis of the plug member 23. Also, the upstream and downstream ends of the plug member 23 are advantageously tapered as shown in FIGS. 3 and 4. The plug member 23 preferably fits securely within beveled ends of the flow passage which is formed between the end caps 16a and 16b. The tapered ends of the plug member 23 are received in beveled receptacles in the hub 16f and at the inside base of the cylindrical extension 16f. The beveled receptacles are formed symmetrically about the axis of the first passage, and, thus, when the tapered end of the plug member 23 is received therein, the bore 24 of plug members 23 is maintained in axial alignment with the bores 16c and 16d in end cap 16a and 16b, respectively. As shown in FIGS. 4 and 5, the beveled receptacle in the base of the cylindrical extension 16f has three undercut slots 16h in the beveled surface and positioned equidistantly therearound. This leaves three equally spaced beveled ribs 16j upon which the tapered end of the plug member 23 seats. Fluid flow communication is established from the flow passage around the plug member 23 to the passage 16d in end cap 16b via way of the undercut slots 16h. The beveled receptacle in hub 16e at the other end of the plug member 23 is of the same basic construction as the beveled receptacle shown in FIGS. 4 and 5, with the upstream, tapered end of the plug member 23 adapted to seat on the beveled ribs, so that fluid flow communication is established from the passage 16c in the end cap 16a to the flow space 24 around the plug member 23 via way of the undercut slots 16h.

In use, the flow device of this invention is efficient, reliable, and easy to manipulate. Prior to the insertion of the catheter into an artery or vein of the patient, the flow device of this invention is connected between the catheter and a source of medical fluid. The medical fluid can be contained in a pressurized vessel, or a container which is elevated sufficiently above the patient so as to provide for the working upstream pressure necessary for proper flow of fluid through the bore 25 of the device.

All air bubbles are eliminated from the catheter system by squeezing the flexible tube 22, thereby flushing the system with a relatively large flow of fluid which flows past the valve plug 23. When all air bubbles have been eliminated, the squeezing action on tube 22 is terminated and the relative large flow of fluid stops, with only the limited, small flow of fluid through the second passage or bore 25 continuing. The catheter is then inserted into the patient's body, with the small flow of fluid passing through the catheter into the vein or artery of the patient. This continuous flow of fluid through the catheter reduces the occurrence of blood clotting or other occlusions occurring in the end of the catheter positioned within the patient's body.

The fitting 21 on the end cap 16b of the flow control device is, of course, connected to whatever indicating or recording means is desired, or to a pressure transducer for oscilloscopic observations. To assure quality of the information obtained from the catheter system, the system is manually flushed from time to time with a relatively rapid flushing flow of fluid by simply squeezing the flexible tube 22 of the flow control apparatus to permit fluid to flow around the valve plug 23. When the squeezing action is terminated the relatively rapid flow of fluid through the catheter stops, and the smaller flow of fluid from the bore 24 continues in its normal course. The periodic flushing of the catheter systems is accomplished quickly and easily, using only one hand of the person handling the apparatus.

The device of this invention can also be advantageously used in combination with a stopcock downstream of the unit 10 to obtain blood samples from the patient or to infuse a desired amount of medication or blood samples to the patient without requiring a second catheterization, cannulation or hypodermic injection of the patient.

It has been found that the cylindrical extension 16f positioned around the portion of the plug member 23 downstream from the raised band 23a on the plug member 23 has a significant beneficial effect on the wave forms and other clinical data produced by monitoring apparatus attached to the device by way of fitting 21. Restraining the movement of the plug member 23 at both of its ends also has a beneficial effect on the wave forms and other clinical data produced by the monitoring apparatus.

Although the apparatus has been shown and described in connection with a catheter system wherein the catheter is placed in the arm of a patient, it is to be understood that the catheter may be entered into various veins or arteries of the body as the general medical situation requires. It is further to be understood that the present disclosure, including the detailed description of a preferred embodiment of the invention, is made by way of example and that various other embodiments are possible without departing from the subject matter coming within the scope of the following claims, which subject matter is regarded as the invention.

I claim:

1. A flow regulating device which provides a continuous regulated flow of a medical fluid to an intravenous catheter system used in monitoring arterial functions and in the infusion of medical fluids to an artery or vein, and which also provides for an intermittent, manually controlled, larger flushing flow of fluid to the catheter system, said device comprising a control member having an inlet means adapted to be connected to a source of a medical fluid and an outlet means adapted to be connected to an intravenous catheter; a first passage connecting said inlet and outlet means for fluid communication therebetween, said first passage at least in part comprising a section of flexible conduit fitting coaxially over a cylindrical, hollow extension which extends from said outlet means to about the midsection of said flexible conduit; valve means comprising a substantially cylindrical plug member positioned coaxially within said flexible conduit and having a raised band around the plug member intermediate its ends, said band being positioned adjacent to the extending end of said cylindrical, hollow extension, said band also being of sufficient diameter to form a substantially flow tight seal with the interior wall of said flexible conduit when the flexible conduit is not being squeezed, so that fluid cannot flow around said plug member, and whereby when said flexible conduit is squeezed, it deforms to create the flow channels extending across the band on said plug member, so that said larger, flushing flow of fluid can flow around said plug member and through said first passage; and a second passage by-passing said valve said valve means and connecting said inlet and outlet means, said second passage containing flow restriction means which limits the flow of fluid therethrough, under a given pressure, to a desired amount.

2. Apparatus in accordance with claim 1, wherein said outlet means is provided with one fitting adapted to be connected to the intravenous catheter and another fitting adapted to be connected to diagnostic apparatus for monitoring arterial parameters.

3. Apparatus in accordance with claim 1, wherein said inlet means comprises a flexible tube anchored at one end to said control member in flow communication with said first passageway therein, said tube having a fitting on its other end for connection to a source of medical fluid.

4. Apparatus in accordance with claim 1, wherein said second passage comprises a bore extending longitudinally through said plug thereby by-passing the valve means in said first passageway.

5. Apparatus in accordance with claim 4, wherein said control member includes a solid body member adjacent to the longitudinal side of said flexible conduit, said body member having concave depressions, respectively, in the side facing the flexible conduit and the two sides extending from the flexible conduit, which form finger guides on each side of the control member to position one's fingers for squeezing the flexible conduit.

6. Apparatus in accordance with claim 4, wherein the flow restriction means in said second passage is provided by at least a portion of said bore having a very small diameter which will limit the flow of fluid under a given pressure through said bore to a desired amount.

7. Apparatus in accordance with claim 4, wherein the flow restriction means in said second passage is provided by positioning a flow resistor in the form of a marine-bore capillary tube in said second passage.

8. Apparatus in accordance with claim 4, wherein said second passage extends coaxial with the longitudinal axis of said plug.

9. Apparatus in accordance with claim 7, wherein the downstream end of said plug is tapered, and the interior of the first passage adjacent to the downsteam end of said plug is flared outwardly symmetrically about the axis of said first passage so as to receive the tapered downstream end of said plug, whereby the downstream end of said plug and the outlet of said second passage is maintained in axial alignment with said first passage.

10. Apparatus in accordance with claim 9, wherein the flared portion of the downstream end of said first passage has at least one undercut groove extending therealong which establishes a flow channel between said first passage and said outlet means when the tapered downstream end of said plug is engaged in the flared downstream end of said first passage.

11. Apparatus in accordance with claim 9, wherein the upstream end of said plug is tapered, and the interior of the first passage adjacent to the upstream end of said plug is flared outwardly symmetrically about the axis of said first passage so as tto receive the tapered upstream end of said plug, whereby the upstream end of said plug and the inlet of said second passage is maintained in axial alignment with said first passage.

12. Apparatus in accordance with claim 9, wherein the flared position of the upstream end of said first passage has at least one undercut groove extending therealong which establishes a flow channel between said first passage and said inlet means when the tapered upstream end of said plug is engaged in the flared, downstream end of said first passage.

* * * * *